United States Patent [19]

Sjogreen et al.

[11] Patent Number: 5,324,863

[45] Date of Patent: Jun. 28, 1994

[54] PROCESS FOR THE PRODUCTION OF DI-TRIMETHYLOLPROPANE

[75] Inventors: Carl-Axel Sjogreen, Perstorp; Goran Axelsson, Hassleholm, both of Sweden

[73] Assignee: Perstorp AB, Perstorp, Sweden

[21] Appl. No.: 30,020

[22] PCT Filed: Sep. 9, 1991

[86] PCT No.: PCT/SE91/00589

§ 371 Date: Mar. 24, 1993

§ 102(e) Date: Mar. 24, 1993

[87] PCT Pub. No.: WO91/10633

PCT Pub. Date: Jul. 25, 1991

[30] Foreign Application Priority Data

Sep. 24, 1990 [SE] Sweden .............................. 9003016-4

[51] Int. Cl.$^5$ ......................... C07C 41/09; C07C 43/10
[52] U.S. Cl. ................................. 568/680; 560/263
[58] Field of Search ......................... 568/680; 560/263

[56] References Cited

U.S. PATENT DOCUMENTS

| | | | |
|---|---|---|---|
| 3,670,013 | 6/1972 | Leibfried | 560/263 |
| 3,673,226 | 6/1972 | Malec | 260/410.6 |
| 3,681,440 | 8/1972 | Gash | 560/263 |
| 3,829,507 | 8/1974 | Zey | 568/680 |
| 3,968,169 | 7/1976 | Seiden et al. | 568/680 |
| 5,254,749 | 10/1993 | Kambara et al. | 568/680 |

FOREIGN PATENT DOCUMENTS

| | | |
|---|---|---|
| 2358297 | 5/1974 | Fed. Rep. of Germany . |
| 3340791 | 5/1985 | Fed. Rep. of Germany . |
| 8705 | 6/1960 | Japan .................................. 568/680 |
| 1291335 | 10/1972 | United Kingdom . |
| 9110633 | 7/1991 | World Int. Prop. O. . |
| 5134 | 4/1992 | World Int. Prop. O. .......... 568/680 |

OTHER PUBLICATIONS

Wagner et al, "Synthetic Organic Chemistry", pp. 169 and 486.

*Primary Examiner*—Joseph E. Evans
*Attorney, Agent, or Firm*—Stevens, Davis, Miller & Mosher

[57] ABSTRACT

Process for the production of di-trimethylolpropane (di-TMP), which comprises subjecting a solution containing less than 3 per cent by weight, preferably less than 1 per cent by weight of water, free trimethylolpropane (TMP) and/or partial ester between TMP and a monocarboxylic acid or its anhydride having 1-4 carbon atoms in the chain, which partial ester on average contains 1.0-2.5, preferably 1.0-2.0 ester groups per molecule to an etherification reaction by heating to 50°-200° C., preferably 70°-190° C. in the presence of an acid catalyst in solid state or in dissolved state until at most 30%, preferably at most 15% of the total content of free TMP and partial ester of TMP in the solution has been etherified to free di-TMP and partial ester of di-TMP respectively, at the same time continuously removing etherification water formed at the etherification reaction under vacuum at a pressure of 0.1-200 mm Hg, preferably 0.1-50 mm Hg or by an azeotropic distillation by means of a compound such as hexane, toluene, xylene or the like forming an azeotropic mixture, and recovering free di-TMP and di-TMP bonded as a partial ester respectively from the reaction mixture in a suitable way.

12 Claims, No Drawings

PROCESS FOR THE PRODUCTION OF DI-TRIMETHYLOLPROPANE

The present invention relates to a process for the production of di-trimethylolpropane (di-TMP).

Usually trimethylolpropane (TMP) is produced by a reaction between n-butyraldehyde and formaldehyde in an alkaline aqueous solution, for instance containing sodium hydroxide or calcium hydroxide. At the reaction also oligomers of TMP such as di-TMP, tri-TMP and higher oligomers are formed. Depending on the reaction conditions these oligomers are formed in a higher or lower degree.

For certain purposes it is desirable to produce a pure di-TMP. Di-TMP has for instance a considerable use as a component in binders for paint and resins, photo curing resins, PVC stabilizers etc.

Pure di-TMP can be produced by isolation from the reaction mixture obtained by the normal TMP production. However, this process has several disadvantages. For instance, the process for production and purification of the di-TMP will be complicated. The energy consumption will also be high. In addition the content of di-TMP obtained will be rather moderate even if the TMP process is set to give a maximal yield of di-TMP. Thus, usual TMP-processes cannot meet an increasing demand of di-TMP.

In the U.S. Pat. No. 3,673,226 a process for the production of a synthetic lubricant is shown. Then di-TMP is produced in a first etherification reaction from TMP in a process using an acid catalyst. The reaction is carried out discontinuously at atmospheric pressure during removal of water by means of distillation in the presence of toluene. The known discontinuous process gives low yields since the di-TMP formed is partially further etherified to tri-TMP and other higher oligomers. A number of side reactions also take place.

According to the U.S. patent the di-TMP obtained is totally esterified in a second step. The fully esterified product is then used as a partial component of a synthetic lubricant.

Thus, the usual TMP-process as well as the process according to the U.S. Pat. No. 3,673,226 have drawbacks concerning the production of di-TMP.

According to the present invention it has quite surprisingly been possible to avoid the above disadvantages and bring about a process for the production of di-trimethylolpropane (di-TMP).

The process comprises subjecting a solution containing less than 3 per cent by weight, preferably less than 1 per cent by weight of water, free trimethylolpropane (TMP) and/or a partial ester between TMP and a monocarboxylic acid or its anhydride having 1-4 carbon atoms in the chain, which partial ester on average contains 1.0-2.5, preferably 1.0-2.0 ester groups per molecule, to an etherification reaction by heating to 50°-200° C., preferably 70°-190° C. in the presence of an acid catalyst in a solid state or in a dissolved state until at most 30%, preferably at most 15% of the total content of free TMP and partial ester of TMP in the solution has been etherified to free di-TMP and partial ester of di-TMP respectively, at the same time continuously removing etherification water formed at the etherification reaction at vacuum at a pressure of 0.1-200 mm Hg, preferably 0.1-50 mm Hg or by an azeotropic distillation by means of a compound such as hexane, toluene, xylene or the like forming an azeotropic mixture, and recovering free di-TMP and di-TMP bonded as a partial ester respectively from the reaction mixture in a suitable way.

The acid catalyst used can for instance consist of alkanesulphonic acids such as methane sulphonic acid, aromatic sulphonic acids such as xylene sulphonic acid and p-toluene sulphonic acid as well as sulphuric acid and phosphoric acid and other inorganic and organic acids with a pKs value <4. Also Lewis acids may be used as catalysts. However, according to the invention a catalyst in solid state is often preferred. In this case the catalyst may be present for example as granules, grains, tablets or powder.

As a solid acid catalyst an aromatic polymer containing sulphonic acid groups can be used. One example of such a suitable polymer is a cation exchanging resin in acid form consisting of sulphonated polystyrene copolymer marketed by Rohm and Haas Company under the name Amberlyst 15.

The solid acid catalyst can also consist of a perfluoroalkane polymer with sulphonic acid groups or an inorganic catalyst of zeolite type for instance.

It is especially preferable if the solid inorganic acid catalyst is porous. The pore diameter should then be at least 8Å.

The inorganic catalyst can also consist of a stratified material. Then the channels between the layers are suitably at least 8Å.

The partial ester of TMP and a monocarboxylic acid used according to the invention preferably consists of a reaction product of TMP and formic acid, acetic acid, acetic anhydride, propionic acid, propionic anhydride burytic acid or butyric anhydride. Only one or a mixture of two or more such acids or anhydrides can be used at the production of the partial ester of TMP. Besides said production is known per se.

At the etherification reaction according to the invention etherification water is formed. As mentioned above the water content of the reaction mixture should be kept lower than 3 per cent by weight, preferably lower than 1 per cent by weight calculated on the whole mixture. According to the invention it has namely been possible to establish that a higher water content disturbs the etherification reaction and decreases the yield of free di-TMP and di-TMP bonded as partial ester.

During the synthesis the water content can continuously be kept at a desired low value by carrying out the synthesis at a pressure of 0.1-200 mm Hg preferably 0.1-50 mm Hg and most preferably 0.1-20 mm Hg, whereby water escapes from the reaction mixture.

As mentioned above the temperature during the reaction is suitably 50°-200° C. preferably 70°-190° C. In many cases it has turned out that the interval 140°-180° C. is especially preferable together with a pressure of 0.1-15 mm Hg.

The water content can also be reduced if the synthesis is performed in contact with a water absorbing agent, for example a molecular sieve or another solid drying agent.

It is essential according to the invention that the reaction is only run until at most 30%, preferably at most 15% of the total content of free TMP and partial ester of TMP in the solution has been esterified to free di-TMP and partial ester of. di-TMP respectively. By keeping the conversion degree at this low level it is namely possible to limit the formation of trimer and higher oligomers of TMP.

The reaction mixture obtained contains di-TMP, TMP and minor amounts of tri-TMP. Possibly they are all present in both free and esterified form. Small amounts of other by-products may also be present. There are many alternatives available for recovering the desired product di-TMP. One suitable first step is to remove the more low boiling products TMP and its esters and certain by-products by distillation. Then the by-products can be withdrawn as a special fraction and TMP and its esters can be used as raw material for the next synthesis.

At a preferred embodiment of the invention the etherification synthesis and the above separation of low boiling products are carried out continuously in such a way that the reaction is allowed to take place by feeding the initial solution through a solid catalyst bed. Then the reaction mixture is distilled whereby TMP and its esters are returned to the reactor.

Such a continuous process is also extremely suitable by the direct etherification of TMP where the starting material is not a partial ester of TMP but TMP. The above mentioned catalysts, temperatures, pressures etc used in the etherification of the partial esters of TMP can also be used in this direct etherification. In comparison with a discontinuous direct etherification of TMP for example according to the above U.S. Pat. No. 3,673,226 a continuous process gives a considerably higher yield.

There are several alternatives for obtaining di-TMP from the reaction mixture which previously has been liberated from volatile components as described above. For example di-TMP and its esters can be distilled off from tri-TMP and its esters and the other high boiling products. Thereafter suitably a hydrolysis of the fraction consisting of di-TMP and its esters is carried out by the action of water on the mixture during an acid catalysis. The liberated carboxylic acid can then be used for the next synthesis of the partial ester of TMP.

In principle the above acid hydrolysis can be replaced by an alkaline hydrolysis. However, such an alkaline hydrolysis has the disadvantage that the corresponding carboxylate is formed as a by-product. Either the carboxylate has to be purified and sold or converted the corresponding acid for recirculation to the step with partial esterification.

The di-TMP thus liberated from ester groups can now be obtained as a rest from the solution by evaporation of water. Di-TMP is obtained as a melt which is transferred to solid state for instance by flaking. If desired the di-TMP can be further purified by redistillation of the melt first.

Di-TMP can also be recovered by diluting the solution with water after the above hydrolysis and crystallizing the di-TMP by cooling.

The invention will be explained further in connection with the embodiment examples below of which example 1 relates to a comparison test outside the scope of the invention. Examples 2, 8 and 9 illustrate an embodiment according to the invention where TMP is directly etherified under vacuum. Examples 3 and 4 show the preparation of a partial ester of TMP, which ester is then used as a starting material at another embodiment of the invention illustrated in examples 5-7.

EXAMPLE 1

Reproduction of U.S. Pat. No. 3,673,226, example 1.

268 g TMP (=2.0 moles) and 150 g toluene were charged into a flask provided with a stirrer, a thermometer, a heating mantle and a water separator according to Dean-Stark. 2 g p-toluene sulphonic acid was added. The mixture was heated while stirring to 200° C., whereby a part of the toluene was distilled off. The mixture was refluxed at this temperature until 18 g water had separated by means of the separator. The mixture was cooled to 100° C. and neutralized with 1-n NaOH. Water and toluene were evaporated at 100° C. and 20 mm Hg.

245.6 g yellow brown viscous oil was obtained containing 35.9 g di-TMP, 6.4 g tri-TMP and 116.1 g unreacted TMP. The yield to di-TMP was 25% calculated as di-TMP formed in per cent of TMP consumed and taking into account the amount of reaction water formed.

EXAMPLE 2

Into a flask provided with a heating mantle, a stirrer and a reflux cooler 201 g TMP (=1.5 moles) and 4 g methane sulphonic acid were charged. The mixture was heated to 150° C. at a pressure of 0.5 mm Hg. After 2 hours and 15 minutes 26.1 g di-TMP had formed in the reaction solution which was slightly brown-colored. At the same time there was 2.8 g tri-TMP in the solution. The remaining TMP was 147.6 g. The yield to di-TMP was 52% calculated as di-TMP formed in per cent of TMP consumed and taking into account the amount of reaction water formed. The water content of the solution was less than 0.1%.

EXAMPLE 3

402 g TMP (3.0 moles) and 306 g (3.0 moles) acetic anhydride were charged into a flask provided with a heating mantle, a stirrer and a reflux cooler and heated while stirring to 75° C. After 1 hour at 75° C. the solution was heated to 125° C. and kept there for 4 hours.

The acetic acid formed was evaporated at about 80° C. and a pressure of about 20 mm Hg. The product obtained (531 g) had the following composition:

| TMP | 10% |
| TMP monoacetate | 39% |
| TMP diacetate | 40% |
| TMP triacetate | 11% |

This composition corresponds to an average of 1.52 acetate groups bonded to each TMP molecule.

EXAMPLE 4

335 g TMP (=2.5 moles) and 408 g acetic anhydride (=4 moles) were charged into a flask provided with a heating mantle, a stirrer and a reflux cooler and heated to 75° C. while stirring. After 1 hour at 75° C. the solution was heated to 125° C. and kept there for 4 hours. The acetic acid formed was evaporated at about 80° C. and a pressure of 20 mm Hg. The product obtained (541 g) had the following composition:

| TMP | 1% |
| TMP monoacetate | 19% |
| TMP diacetate | 46% |
| TMP triacetate | 34% |

This composition corresponds to an average of 2.13 acetate groups bonded to each TMP molecule.

EXAMPLE 5

As a raw material 150 g TMP acetate mixture produced according to Example 3 and 30 g acid catalyst, sulphonated styrene polymer in the form of granules (Amberlyst 15, Rohm and Haas) were charged into a flask provided with a heating mantle, a stirrer and a reflux cooler. The synthesis was carried out at a pressure of 0.2-3 mm Hg and a temperature of 100° C. The water formed was distilled off continuously.

After two hours, in all 7.1 g di-TMP in free form and in acetate bonded form had been formed in the reaction solution which was slightly brown-colored. At the same time there was in all 0.38 g tri-TMP, as free tri-TMP and acetate-bonded tri-TMP respectively in the solution. The remaining amount of TMP in free form and in acetate bonded form in the reaction mixture was 91 g. The yield to di-TMP calculated as di-TMP and di-TMP acetate formed in per cent of TMP and TMP acetate consumed was 74% taking into account the amount of reaction water formed. The water content of the solution was less than 0.1%.

EXAMPLE 6

The reaction was carried out according to Example 5 with the difference that the reaction time was only 1 hour. After the reaction, there was 4.7 g di-TMP in free form and in acetate bonded form in the reaction solution which was slightly yellow-colored. At the same time, 0.24 g tri-TMP in free form and in acetate-bonded form had been formed. The yield to di-TMP was 83% calculated in the same way as in Example 5. The remaining amount of TMP in free form and in acetate-bonded form in the reaction solution was 96 g. The water content of the solution was less than 0.1%.

EXAMPLE 7

The reaction was carried out according to Example 5 with the difference that 150 g TMP-acetate mixture produced according to Example 4 was used as raw material. After two hours 3.9 g di-TMP in free form and in acetate bonded form had been formed in the reaction solution which was slightly brown colored. At the same time 0.15 g tri-TMP in free form and in acetate bonded form had been formed. The remaining amount of TMP in free form and in acetate-bonded form in the reaction solution was 85 g. The yield to di-TMP was 78% calculated in the same way as in Example 5. The water content of the solution was less than 0.1%.

EXAMPLE 8

1210 g TMP and 0.62 g sulphuric acid were charged into a flask provided with a heating mantle, a stirrer and a reflux cooler.

The apparatus was set on a pressure of 6 mm Hg. The mixture was heated to a temperature of 160°-165° C. After 4 hours 90.0 g di-TMP had been formed in the reaction solution. At the same time there was 5.9 g tri-TMP in the solution. The remaining TMP in the reaction solution was 1047 g. The yield to di-TMP was 59% calculated in the same way as in Example 2.

EXAMPLE 9

53.6 g TMP and 2.22 g Nafion ® were charged into a flask provided with a heating mantle, a reflux cooler and a stirrer. Nafion ® is a solid acid catalyst in the form of granules consisting of a perfluoroalkane polymer with sulphonic acid groups. Nafion ® is manufactured by Du Pont Company, USA.

The mixture was heated to 155° C. at a pressure of 4 mm Hg and kept there for 3 hours. Then 2.7 g di-TMP had been formed in the reaction solution. The remaining TMP was 46.6 g. The yield to di-TMP was 41% calculated as di-TMP formed in per cent of TMP consumed taking into account the amount of reaction water formed. The water content of the solution was less than 0.1%.

The invention is not limited to the embodiments shown since these can be modified in different ways within the scope of the invention.

We claim:

1. A process for production of di-trimethylolpropane (di-TMP) comprising subjecting a reaction mixture containing free trimethylolpropane (TMP) and/or a partial ester of TMP and a monocarboxylic acid or anhydride having 1-4 carbon atoms, which partial ester on average contains 1.0-2.5 ester groups per molecule, to an etherification at a temperature of 50°-200° C. and in the presence of an acid catalyst, until at most 30% of the total content of free TMP or partial ester of TMP is etherified to free di-TMP or partial ester of TMP;

continuously removing etherification water formed during the etherification either under a vacuum of 0.1-200 mm Hg or by means of an azeotropic distillation, while maintaining the water content of the reaction mixture lower than 3% by weight; and recovering formed free di-TMP; or obtaining di-TMP as output of an acid hydrolysis of the formed di-TMP partial ester and thereafter recovering such di-TMP.

2. The process according to claim 1, wherein the catalyst is solid and present as granules, grains, tablets or powder.

3. Process according to claim 2, wherein the catalyst is porous.

4. The process according to claim 2, wherein the catalyst consists of an aromatic polymer containing sulphonic acid groups, a perfluoroalkane polymer with sulphonic acid groups or an inorganic catalyst of zeolite type.

5. The process according to claim 1, wherein di-TMP is recovered from the output after a preceding removal of low boiling products by distillation.

6. The process according to claim 1, wherein a partial ester between TMP and acetic acid or acetic anhydride is used.

7. The process according to claim 1, wherein the etherification is carried out at a vacuum of 0.1-15 mm Hg and a temperature of 140°-180° C.

8. The process according to claim 1, wherein the water content is maintained at lower than 1% by weight.

9. The process according to claim 1, wherein the partial ester of di-TMP contains an average of 1.0-2.0 ester groups per molecule.

10. The process according to claim 1, wherein at most 15% of the total content of free TMP or partial ester of TMP is etherified to free di-TMP or partial ester of di-TMP.

11. The process according to claim 1, wherein the continuous water removal is performed under a vacuum of 0.1-50 mm Hg.

12. The process according to claim 1, wherein the azeotropic distillation is performed using hexane, toluene or xylene as an azeotropic solvent.

* * * * *